(12) United States Patent
Hong et al.

(10) Patent No.: US 10,962,522 B2
(45) Date of Patent: *Mar. 30, 2021

(54) METHOD FOR PREDICTING PHYSICAL PROPERTIES OF POLYMERS

(71) Applicant: LG Chem, Ltd., Seoul (KR)

(72) Inventors: Yoon Ki Hong, Daejeon (KR); Hyuck Ju Kwon, Daejeon (KR); Eun Kyoung Song, Daejeon (KR); Dae Sik Hong, Daejeon (KR); Ye Jin Lee, Daejeon (KR); Joong Soo Kim, Daejeon (KR); Eun Young Shin, Daejeon (KR); Young Suk You, Daejeon (KR); Ki Soo Lee, Daejeon (KR)

(73) Assignee: LG Chem, Ltd.

( * ) Notice: Subject to any disclaimer, the term of this patent is extended or adjusted under 35 U.S.C. 154(b) by 261 days.

This patent is subject to a terminal disclaimer.

(21) Appl. No.: 15/768,968

(22) PCT Filed: Oct. 12, 2017

(86) PCT No.: PCT/KR2017/011253
§ 371 (c)(1),
(2) Date: Apr. 17, 2018

(87) PCT Pub. No.: WO2018/097476
PCT Pub. Date: May 31, 2018

(65) Prior Publication Data
US 2020/0132661 A1  Apr. 30, 2020

(30) Foreign Application Priority Data

Nov. 24, 2016 (KR) ........................ 10-2016-0157724

(51) Int. Cl.
*G01N 33/44* (2006.01)
*G01N 30/86* (2006.01)
*G01N 30/00* (2006.01)

(52) U.S. Cl.
CPC ....... *G01N 33/442* (2013.01); *G01N 30/8606* (2013.01); *G01N 2030/486* (2013.01)

(58) Field of Classification Search
CPC ............. G01N 33/442; G01N 30/8606; G01N 2030/486
See application file for complete search history.

(56) References Cited

U.S. PATENT DOCUMENTS 4,183,793 A * 1/1980 Balko ....................... C25B 1/46
204/296
7,642,330 B2   1/2010 Mathews et al.
(Continued)

FOREIGN PATENT DOCUMENTS

CN   103608364 A   2/2014
CN   104583300 A   4/2015
(Continued)

OTHER PUBLICATIONS

Ahmed et al., "The experimental observation and numerical prediction of planar entry flow and die swell for molten polyethylenes", J. Non-Newtonian Fluid Mech., vol. 59, pp. 129-153, Feb. 1995.
(Continued)

*Primary Examiner* — Nimeshkumar D Patel
*Assistant Examiner* — Gedeon M Kidanu
(74) *Attorney, Agent, or Firm* — Lerner, David, Littenberg, Krumholz & Mentlik, LLP

(57) ABSTRACT

The present invention relates to a method for predicting the physical properties of polymers. More specifically, the present invention relates to a method for predicting the processability of polymers using a molecular weight distribution curve.

5 Claims, 2 Drawing Sheets

(56) References Cited

U.S. PATENT DOCUMENTS

| | | | |
|---|---|---|---|
| 8,114,946 B2* | 2/2012 | Yang | C08F 210/16 526/129 |
| 8,311,787 B2 | 11/2012 | Ganvir et al. | |
| 8,536,081 B2* | 9/2013 | Jacobsen | C08F 10/00 502/113 |
| 9,023,959 B2* | 5/2015 | McDaniel | C08F 210/16 526/129 |
| 9,441,063 B2* | 9/2016 | Cruz | C08F 4/6592 |
| 9,493,589 B1 | 11/2016 | Greco et al. | |
| 10,358,509 B2* | 7/2019 | Fraaije | C08F 10/02 |
| 2002/0123848 A1 | 9/2002 | Schneiderman et al. | |
| 2005/0240385 A1* | 10/2005 | Xie | G01N 30/78 703/11 |
| 2006/0189775 A1* | 8/2006 | Takahashi | C08F 297/08 526/352 |
| 2012/0172548 A1* | 7/2012 | Cho | C08F 210/16 526/64 |
| 2012/0316311 A1* | 12/2012 | Yang | C08L 23/0815 526/348.2 |
| 2014/0045988 A1* | 2/2014 | Dotsch | C08F 2/001 524/528 |
| 2015/0159002 A1* | 6/2015 | Cermelli | C08L 23/06 525/240 |
| 2015/0259455 A1 | 9/2015 | Hlavinka et al. | |
| 2016/0130376 A1* | 5/2016 | Mihan | C08F 10/02 526/154 |
| 2016/0152747 A1* | 6/2016 | Meier | C08L 23/0815 526/124.2 |
| 2016/0222144 A1 | 8/2016 | Kum et al. | |
| 2016/0272743 A1* | 9/2016 | Park | B01J 31/143 |
| 2017/0066857 A1 | 3/2017 | Greco et al. | |
| 2018/0334558 A1* | 11/2018 | Fellahi | C08K 7/14 |
| 2019/0064051 A1* | 2/2019 | Hong | B29C 49/00 |
| 2019/0309107 A1* | 10/2019 | Meier | C08F 110/02 |

FOREIGN PATENT DOCUMENTS

| | | |
|---|---|---|
| CN | 104910305 A | 9/2015 |
| JP | H07188342 A | 7/1995 |
| JP | 2004514902 A | 5/2004 |
| KR | 100947718 B1 | 3/2010 |
| KR | 20140033083 A | 3/2014 |
| KR | 20150037591 A | 4/2015 |
| KR | 20150057996 A | 5/2015 |
| WO | 2006107374 A1 | 10/2006 |

OTHER PUBLICATIONS

Fujiyama et al., "Rheological Properties of Polypropylenes with Different Molecular Weight Distribution Characteristics", Journal of Applied Polymer Science, vol. 84, pp. 2128-2141, Jul. 2001.

Giurco et al., "The Influence of Molecular Characteristics of Synthetic Rubbers on Mixing and Extrusion Behavior", J. Polymer Science.: Symposium, No. 55, 1976, pp. 25-37.

International Search Report for Application No. PCT/KR2017/011253 dated Jan. 22, 2018.

Liang., "Data Interpretation: Estimation of die-swell ratio for polymer melts from exit pressure drop data", Polymer Testing, vol. 20, pp. 29-31, Nov. 1999.

Nithi-Uthai et al., "Numerical Studies of the Effect of Constitutive Model Parameters As Reflecting Polymer Molecular Structure on Extrudate Swell", Applied Rheology, vol. 12, Aug. 2002, pp. 252-259.

Seriai et al., "A simple model to predict extrudate swell of polystyrene and linear polyethylenes", Rheologica Acta, vol. 32, No. 6, pp. 532-538, Oct. 1993.

Extended European Search Report including Written Opinion for Application No. EP17861170.3 dated Feb. 12, 2019.

L. Wild et al: "Influence of long-chain branching on the viscoelastic properties of low-density polyethylenes", Polymer Engineering and Science, Dec. 1976, vol. 16, No. 12, pp. 811-816, XP055550677.

Allain et al., "Experimental investigation and scaling law analysis of die swell in semi-dilute polymer solutions", Journal of Non-Newtonian Fluid Mechanics, Nov. 1997, vol. 73, Issues 1-2, pp. 51-66.

Chinese Search Report for Application No. CN 201780003944.6 dated Apr. 10, 2020, 4 pages.

Ma, Tianmin, "The effects of molecular weight and molecular weight distribution on the elasticity of polypropylene and polystyrene melts", Plastics, Aug. 1979, vol. 4, pp. 61-68. English language translation of Abstract included only.

* cited by examiner

METHOD FOR PREDICTING PHYSICAL PROPERTIES OF POLYMERS

CROSS-REFERENCE TO RELATED APPLICATION(S)

This application is a national phase entry under 35 U.S.C. § 371 of International Application No. PCT/KR2017/011253, filed Oct. 12, 2017, which claims priority to Korean Patent Application No. 10-2016-0157724, filed Nov. 24, 2016, the disclosures of which are incorporated herein by reference.

BACKGROUND OF THE INVENTION

Field of the Invention

The present invention relates to a method for predicting physical properties of polymers. More specifically, the present invention relates to a method for predicting the processability of polymers using a molecular weight distribution curve.

Description of the Related Art

Polyolefin resins used for large-diameter high-pressure pipe tubes generally require high pressure resistance characteristic and excellent processability. The high pressure resistance characteristic is generally a physical property that can be expressed in a high density region, and this is because the higher the degree of crystallization in the polyolefin resin, the modulus increases and thus the strength to withstand high pressure increases.

However, generally, pipes has to assure a long-term pressure resistance stability for at least 50 years, but there is a disadvantage that, if the density is high, the resistance against the brittle fracture mode is deteriorated and the long-term pressure resistance characteristic is deteriorated. In addition, when the molecular weight is low or the molecular weight distribution is narrow, the large diameter pipe is difficult to process due to the occurrence of sagging phenomenon during processing. Consequently, the polyolefin resin having a high molecular weight and a very broad molecular weight distribution should be applied to solve these problems. Especially, if the molecular weight is high, extrusion load is largely generated and pipe appearance is poor, and thus a very wide molecular weight distribution is necessarily required.

Although many attempts have been conducted to improve these problems, there is a problem that the physical properties and processability of the product are not satisfied at the same time. Therefore, manufacture of a superior product having a balance between long-term stability and processability is constantly required.

On the other hand, the processability of the polyolefin resin can be evaluated by a die swell ratio. The die swell ratio requires expensive analytical instruments for measurement, and the measurement error is relatively large, which is a hurdle to the development of a new resin for high-pressure pipes.

SUMMARY OF THE INVENTION

The present invention has been made in view of the above problems, and it is an object of the present invention to provide a method capable of evaluating physical properties which are associated with the processability and dimensional stability, among the physical properties of polymers, by using a molecular weight distribution curve of polymers with high reliability.

In order to achieve the above object, the present invention provides a method for predicting physical properties of polymers comprising the steps of:

measuring a molecular weight distribution curve of the polymer to be measured (herein, a log value of a molecular weight MW (log MW) is denoted by x-axis, and a molecular weight distribution to the log value (dwt/d log MW) is denoted by y-axis) using a gel permeation chromatography (GPC) at a temperature of 160° C.;

dividing the section between 3.0 and 7.0 on the x-axis of the molecular weight distribution curve into four equal parts to obtain the integral value of the molecular weight distribution curve at each section; and predicting a die swell ratio value from the integral value.

According to the present invention, there may be provided a method capable of evaluating physical properties which are associated with the processability and dimensional stability, among the physical properties of polymers, and which require expensive analytical instruments for measurement, by using a molecular weight distribution curve of polymers with high reliability.

DETAILED DESCRIPTION OF THE EMBODIMENTS

Figure 1:
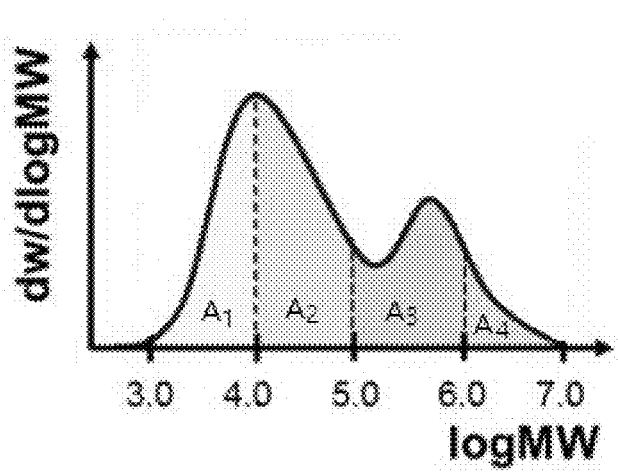
FIG. 1 is a molecular weight distribution curve (GPC curve) measured to predict the physical properties of polymers according to an embodiment of the present invention.

In the present invention, the terms such as "first", "second", etc. are used to describe various components, and the terms are used only for the purpose of distinguishing one component from another.

Moreover, the terminology used herein is for the purpose of describing exemplary embodiments only and is not intended to limit the present invention. Further, singular expressions "a", "an", and "the" used herein may include plural expressions unless the context clearly indicates otherwise. In addition, it should be understood that the meaning of the term "comprising", "including", "having" and the like is intended to specify the presence of stated features, numbers, steps, components or combinations thereof and does not exclude existence or addition of one or more other features, numbers, components or combinations thereof.

The invention can make various modifications and take various forms, and thus specific embodiments are illustrated and described in detail below. It should be understood, however, that the invention is not intended to be limited to any particular disclosure form, but includes all modifications, equivalents and alternatives falling within the spirit and scope of the invention.

Hereinafter, a method for predicting the physical properties of polymers according to specific embodiments of the invention will be described.

According to one embodiment of the present invention, there is provided a method for predicting physical properties of polymers comprising the steps of:

measuring a molecular weight distribution curve of the polymer to be measured (herein, a log value of a molecular weight MW (log MW) is denoted by x-axis, and a molecular weight distribution to the log value (dwt/d log MW) is denoted by y-axis) using a gel permeation chromatography (GPC) at a temperature of 160° C.;

dividing the section between 3.0 and 7.0 on the x-axis of the molecular weight distribution curve into four equal parts to obtain the integral value of the molecular weight distribution curve at each section; and predicting a die swell ratio value from the integral value.

According to one embodiment of the present invention, the predicted value of the die swell ratio may be calculated according to the following Equation 1 using the above integral value:

Die swell ratio, $PV=(-0.136)*A_1+(-0.1152)*A_2+(-0.1033)*A_3+(-0.181)*A_4+13.97$ [Equation 1]

in Equation 1 above, $A_1$ is an integral value of a molecular weight distribution curve in the section where log MW is 3.0 to 4.0, $A_2$ is an integral value of a molecular weight distribution curve in the section where log MW is 4.0 to 5.0, $A_3$ is an integral value of a molecular weight distribution curve in the section where log MW is 5.0 to 6.0, $A_4$ is an integral value of a molecular weight distribution curve in the section where log MW is 6.0 to 7.0, and the integral value of $A_1$ to $A_4$ means a relative value when the integral value of the entire molecular weight distribution curve is 100.

In the present invention, the polymer to be measured may be a polyolefin. Also, the polyolefin may be a polymer or a copolymer obtained by polymerizing one or more monomers selected from the group consisting of ethylene, propylene, 1-butene, 1-pentene, 1-hexene, 4-methyl-1-pentene, 1-octene, 1-decene, 1-dodecene, 1-tetradecene, 1-hexadecene, 1-octadecene, and eicosene.

The polyolefin is a resin obtained by polymerizing an olefin-based monomer such as ethylene in the presence of a catalyst such as metallocene, and is used in various fields due to excellent physical properties.

The physical properties of the polyolefin can be evaluated in several respects. For example, the weight average molecular weight, the number average molecular weight, the molecular weight distribution, the melt flow rate (MFR), the melt flow rate ratio (MFRR), the density, Full Notch Creep Test (FNCT) and the like can be measured and used comprehensively for evaluating the physical characteristics such as strength, processability and stability of polymers.

Among them, a polyolefin resin used in a pressure-resistant heating pipe, a large-diameter high-pressure pipe, or the like is required to have long-term stability under high pressure conditions. As a method of evaluating such processability, a method of measuring the die swell ratio can be mentioned.

Figure 3:
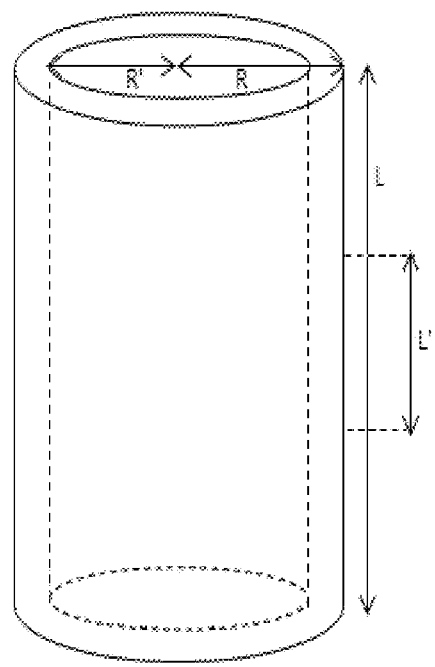
FIG. 3 is a schematic view of an extrusion die for actually measuring the die swell ratio.

FIG. 3 is a schematic view of an extrusion die for actually measuring the die swell ratio.

The die swell ratio can be calculated according to the following Equation 2 by cutting the resin of the middle portion of 20 to 40 cm with scissors and measuring its weight, when the resin coming out through an extrusion die (shown in FIG. 2) of an auto-blow molding m/c (Bloma Engineering, model: BM40DE 70) falls by 60 cm in the vertical direction.

Die Swell Ratio=Weight of Cut Resin (g)/Weight of Reference Resin (g) [Equation 2]

in Equation 2 above, the weight of the cut resin is a weight (unit: g) measured by cutting a resin (length: 20 cm) of the middle portion of 20 to 40 cm with scissors when the resin coming out through an extrusion die (outer diameter: 9 cm, inner diameter: 8.64 cm) falls by 60 cm in the vertical direction, and the weight of the reference resin is a weight (unit: g) corresponding to the resin (length: 20 cm) when the extruded resin has no swell.

That is, referring to FIG. 3, with respect to the total length (L=60 cm) of resin coming out in the form of a pipe via an extrusion die having an outer diameter (R) of 9 cm and an inner diameter (R') of 8.64 cm, the resin (L'=20 cm) of the middle portion of 20 to 40 cm is cut, its weight is measured, and the weight ratio of the reference resin is defined as a die swell ratio. In this case, the weight of the reference resin is a weight corresponding to a length of 20 cm in the resin when the extruded resin is uniformly extruded over the entire length without expansion phenomenon, that is, a weight corresponding to one-third of the total weight of the extruded resin.

However, the method of obtaining the die swell ratio according to the above method requires expensive measuring equipment which causes an increase in the development cost, and the measurement error is relatively large, which makes it difficult to evaluate and analyze the processability of polymers.

Thus, the present inventors have conduced continuous research about a method for evaluating the processability of polymer resins, and found that there is a certain correlation between the integral value for each section of the molecular weight distribution curve (GPC curve) of the polymer resin and the die swell ratio, thereby developing a method for predicting the die swell ratio from the molecular weight distribution curve with a high reliability. The present invention has been completed on the basis of such finding.

That is, it was confirmed that, through measurement of the molecular weight distribution of a polymer resin, particularly a polyolefin resin, the processability and dimensional stability could be predicted beforehand in products manufactured using the polymer resin.

In particular, the method for predicting the physical properties of polymers according to the present invention may be suitable for predicting the physical properties of the polyolefin resin used for the high-pressure pipe. For example, it can be usefully used for a method for predicting a die swell ratio of a polyolefin resin having a high molecular weight and high molecular weight distribution (PDI) in which the weight average molecular weight is 100,000 to 1,000,000 g/mol, or 100,000 to 800,000 g/mol, or 100,000 to 500,000 g/mol and the molecular weight distribution is 5 to 30, or 10 to 30, or 15 to 30.

Hereinafter, a method for predicting physical properties of polymers according to an embodiment of the present invention will be described with reference to the drawings.

FIG. 1 is a molecular weight distribution curve (GPC curve) measured to predict the physical properties of polymers according to an embodiment of the present invention.

First, the molecular weight distribution curve (GPC curve) is obtained for the polymer to be measured at 160° C. using a gel permeation chromatography (GPC). In this case, the log value of the molecular weight MW (log MW) is denoted by x-axis, and the molecular weight distribution to the log value (dwt/d log MW) is denoted by y-axis.

In the x-axis of the molecular weight distribution curve, that is, the log value of the molecular weight (log MW), the section between 3.0 and 7.0 is divided into four equal parts to obtain the integral values of molecular weight distribution curves in each section.

In the above molecular weight distribution curve, when the log MW includes a section deviating from 3.0 to 7.0, the deviating section is excluded, and only the section between 3.0 and 7.0 is divided into four equal parts to obtain the integral value.

Meanwhile, the method for predicting the physical properties of polymers according to the present invention may have a higher reliability when the sum of the integral values ($A_1+A_2+A_3+A_4$) in a section where log MW is 3.0 to 7.0 is close to 100 in the molecular weight distribution curve.

Referring to FIG. 1, the integral value $A_1$ of the molecular weight distribution curve in the section where log MW (x-axis) is 3.0 to 4.0 is obtained. Similarly, the integral value $A_2$ of the molecular weight distribution curve in the section between 4.0 and 5.0, the integral value $A_3$ of the molecular weight distribution curve in the section between 5.0 and 6.0, and the integrated value $A_4$ of the molecular weight distribution curve in the section between 6.0 and 7.0 can be obtained from the GPC curve, respectively. In this case, the integral value of $A_1$ to $A_4$ is used as a relative value when the integral value of the entire molecular weight distribution curve is 100.

The regression analysis was performed by comparing the relative values for each section ($A_1$, $A_2$, $A_3$, $A_4$) obtained from GPC curve as described above with respect to various polymer resins, especially polyolefin resins, with the die swell ratio, and as a result, the following relational equation was derived between the integral value for each section and the die swell ratio.

Die swell ratio, $PV=(-0.136)*A_1+(-0.1152)*A_2+(-0.1033)*A_3+(-0.181)*A_4+13.97$   [Equation 1]

in Equation 1 above, $A_1$ is an integral value of a molecular weight distribution curve in the section where log MW is 3.0 to 4.0 and $A_2$ is an integral value of a molecular weight distribution curve in the section where log MW is 4.0 to 5.0, $A_3$ is an integral value of a molecular weight distribution curve in the section where log MW is 5.0 to 6.0, $A_4$ is an integral value of a molecular weight distribution curve in the section where log MW is 6.0 to 7.0, and the die swell ratio in Equation 1 is a physical property corresponding to the actual measurement value of the die swell ratio obtained by extruding an actual resin using an extrusion die and measuring the degree of expansion.

As a result of verifying the above Equation 1 for a large number of polyolefin resins prepared by various preparation methods, it was found that $R^2$ is 0.8 or more, or 0.9 or more, which is highly reliable.

From the above relational equation, the die swell ratio from the GPC curve, which is relatively easy to measure, can be obtained with high reliability, and it is expected that the cost and time required for evaluating the processability can be greatly reduced. In particular, since the die swell ratio can be predicted only by the GPC curve without additional measurement procedure for a newly developed polymer resin, it is expected that it will contribute greatly to the research and development of a new resin.

Hereinafter, the present invention will be described in more detail by way of examples. However, these examples are presented for illustrative purposes only and the scope of the invention is not limited thereto in any way.

EXAMPLES

Examples 1 to 6

Ten types of polyethylene resins exhibiting various molecular weight distribution curves and having a density in the range of 0.930 to 0.950 g/cm$^3$ were prepared by polymerizing ethylene according to the established method by a metallocene catalyst.

From the molecular weight distribution curve of each polyethylene, the die swell ratio of the polyethylene resin was calculated by the following Equation 1.

Die swell ratio, $PV=(-0.136)*A_1+(-0.1152)*A_2+(-0.1033)*A_3+(-0.181)*A_4+13.97$   [Equation 1]

in Equation 1 above, $A_1$ is an integral value of a molecular weight distribution curve in the section where log MW is 3.0 to 4.0, $A_2$ is an integral value of a molecular weight distribution curve in the section where log MW is 4.0 to 5.0, $A_3$ is an integral value of a molecular weight distribution curve in the section where log MW is 5.0 to 6.0, $A_4$ is an integral value of a molecular weight distribution curve in the section where log MW is 6.0 to 7.0, and the integral value of $A_1$ to $A_4$ means relative values when the integral value of the entire molecular weight distribution curve is 100.

In addition, the actually measured value of the die swell ratio according to Equation 2 and the predicted value of the die swell ratio according to Equation 1 are compared, and the results are shown in Table 1 below.

Figure 2:
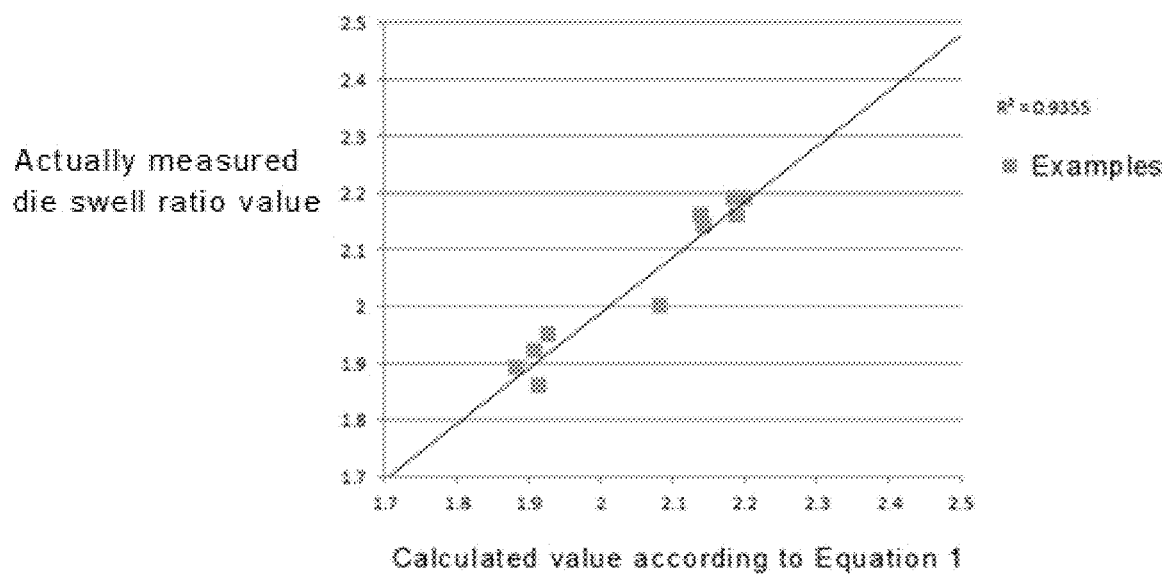
FIG. 2 is a graph showing the relationship between the calculated value and the actually measured value of the die swell ratio according to Equation 1.

Further, the relationship between the calculated value and the actually measured value of the die swell ratio is shown in FIG. 2.

1) Molecular weight distribution curve: Continuous molecular weight distribution was measured using a gel permeation chromatography-FTIR (GPC-FTIR) at a measurement temperature of 160° C., and a log value of the molecular weight MW (log MW) was denoted by x-axis, and the molecular weight distribution to the log MW (dwt/d log MW) was denoted by y-axis, to thereby draw a molecular weight distribution curve.

2) Die Swell Ratio: The die swell ratio can be calculated according to the following Equation 2 by cutting the resin of the middle portion of 20 to 40 cm with scissors and measuring its weight, when the resin coming out through an extrusion die (shown in FIG. 2) of an auto-blow molding m/c (Bloma Engineering, model: BM40DE 70) falls by 60 cm in the vertical direction.

Die Swell Ratio=Weight of Cut Resin (g)/Weight of Reference Resin (g)   [Equation 2]

in Equation 2, the weight of the cut resin is a weight (unit: g) measured by cutting a resin (length: 20 cm) of the middle portion of 20 to 40 cm with scissors when the resin coming out through an extrusion die (outer diameter: 9 cm, inner diameter: 8.64 cm) falls by 60 cm in the vertical direction, and the weight of the reference resin is a weight (unit: g) corresponding to the resin (length: 20 cm) when the extruded resin has no swell.

TABLE 1

|  | Weight average molecular weight (g/mol) | Molecular weight distribution | Integral value for each section of GPC curve | | | | Equation 1 Calculated value (hr) | Actually measured value |
| --- | --- | --- | --- | --- | --- | --- | --- | --- |
|  |  |  | $A_1$ | $A_2$ | $A_3$ | $A_4$ |  |  |
| Example 1 | 327,770 | 25.3633 | 20.32166 | 46.56404 | 21.54408 | 9.325724 | 1.928617 | 1.95 |
| Example 2 | 289,554 | 25.5294 | 24.33681 | 43.46446 | 22.11837 | 8.197844 | 1.884451 | 1.89 |
| Example 3 | 318,468 | 27.2125 | 23.28312 | 41.87206 | 23.68627 | 8.969476 | 1.909568 | 1.92 |
| Example 4 | 387,890 | 16.6455 | 8.937892 | 54.84982 | 22.18146 | 11.05058 | 2.144248 | 2.14 |
| Example 5 | 336,559 | 16.4472 | 11.11483 | 57.50293 | 19.56069 | 9.555881 | 2.083812 | 2.00 |
| Example 6 | 282,228 | 21.7701 | 16.84771 | 46.21066 | 25.3944 | 10.04293 | 1.914232 | 1.86 |
| Example 7 | 352,109 | 10.7814 | 5.549175 | 58.08235 | 24.5495 | 9.882188 | 2.199586 | 2.19 |
| Example 8 | 370,725 | 12.2554 | 6.387199 | 56.98076 | 24.17443 | 10.49551 | 2.140251 | 2.16 |
| Example 9 | 359,399 | 11.5344 | 6.112806 | 55.78383 | 25.68316 | 10.35217 | 2.185548 | 2.19 |
| Example 10 | 366,132 | 10.9130 | 5.516394 | 55.77089 | 25.85677 | 10.685 | 2.189975 | 2.16 |

As shown in Table 1 and FIG. 2, the die swell ratio (PV) value calculated according to Equation 1 of the present invention is a highly reliable predicted value with $R^2=0.9355$ as compared with the actually measured die swell ratio value.

What is claimed is:

1. A method for manufacturing a pipe comprising:
polymerizing one or more olefin monomers in a presence of a catalyst,
forming a polymer resin,
measuring a molecular weight distribution curve of the polymer resin using a gel permeation chromatography (GPC) at a temperature of 160° C., wherein a log value of a molecular weight MW (log MW) is denoted by x-axis, and a molecular weight distribution to the log value (dwt/dlog MW) is denoted by y-axis;
dividing a section between 3.0 and 7.0 on the x-axis of the molecular weight distribution curve into four equal parts to obtain an integral value of the molecular weight distribution curve at each section; and
calculating a predicted value of a die swell ratio value from the integral value, and
manufacturing the pipe using the polymer resin,
wherein the calculating the predicted value of the die swell ratio is performed according to following Equation 1 using the integral value:

Die swell ratio, $PV=(-0.136)*A_1+(-0.1152)*A_2+(-0.1033)*A_3+(-0.181)*A_4+13.97$ [Equation 1]

$A_1$ is an integral value of a molecular weight distribution curve in the section where log MW is 3.0 to 4.0,
$A_2$ is an integral value of a molecular weight distribution curve in the section where log MW is 4.0 to 5.0,
$A_3$ is an integral value of a molecular weight distribution curve in the section where log MW is 5.0 to 6.0,
$A_4$ is an integral value of a molecular weight distribution curve in the section where log MW is 6.0 to 7.0, and
the integral value of $A_1$ to $A_4$ means relative values when an integral value of entire molecular weight distribution curve is 100.

2. The method according to claim 1, wherein the polymer resin is a polyolefin.

3. The method according to claim 2, wherein the polyolefin is a polymer or a copolymer obtained by polymerizing one or more monomers selected from the group consisting of ethylene, propylene, 1-butene, 1-pentene, 1-hexene, 4-methyl-1-pentene, 1-octene, 1-decene, 1-dodecene, 1-tetradecene, 1-hexadecene, 1-octadecene, and eicosene.

4. The method according to claim 2, wherein the polyolefin has a weight average molecular weight of 100,000 to 1,000,000 g/mol.

5. The method according to claim 2, wherein the polyolefin has a molecular weight distribution of 5 to 30.

* * * * *